United States Patent
Cull et al.

(10) Patent No.: US 7,604,607 B2
(45) Date of Patent: Oct. 20, 2009

(54) PERISTALTIC PUMP FITMENT FOR ATTACHMENT TO AN ASPIRANT COLLECTION BAG

(75) Inventors: Laurence J. Cull, Wildwood, MO (US); Bruce Edward Lawton, Rochester, NY (US); Ronald D. Spoor, Penn Yan, NY (US); Aner Gal, Victor, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 879 days.

(21) Appl. No.: 10/674,094

(22) Filed: Sep. 29, 2003

(65) Prior Publication Data

US 2005/0070859 A1    Mar. 31, 2005

(51) Int. Cl.
*A61B 19/00*    (2006.01)
*A61M 1/00*    (2006.01)
(52) U.S. Cl. ............................. 604/8; 604/319; 604/326
(58) Field of Classification Search ................. 604/403, 604/408, 264, 533, 905, 6.15, 6.16, 6.11, 604/35, 65–67, 326, 327, 319
See application file for complete search history.

(56) References Cited

U.S. PATENT DOCUMENTS

| | | | | |
|---|---|---|---|---|
| 3,781,941 A | * | 1/1974 | MacFarland | ................. 15/339 |
| 3,836,287 A | | 9/1974 | Grosholz et al. | ............ 417/306 |
| 4,416,772 A | * | 11/1983 | Sato et al. | .................... 210/137 |
| 4,813,428 A | | 3/1989 | Muraki et al. | ................ 128/721 |
| 4,904,168 A | * | 2/1990 | Cavoto et al. | ............ 417/477.2 |
| 4,930,997 A | * | 6/1990 | Bennett | .................... 417/410.1 |
| 4,963,131 A | * | 10/1990 | Wortrich | ...................... 604/34 |
| 4,976,708 A | * | 12/1990 | Oshiyama | ................... 604/408 |
| 5,125,891 A | | 6/1992 | Hossain et al. | ................. 604/34 |
| 5,897,524 A | | 4/1999 | Wortrich et al. | ............... 604/30 |
| 6,083,195 A | | 7/2000 | Perkins et al. | ................ 604/30 |
| 6,224,583 B1 | | 5/2001 | Perkins et al. | ............... 604/408 |
| 6,319,223 B1 | | 11/2001 | Wortrich et al. | ............... 604/30 |
| 6,358,232 B1 | * | 3/2002 | Hand et al. | .................. 604/319 |
| 6,561,999 B1 | | 5/2003 | Nazarifar et al. | .............. 604/30 |
| 6,723,110 B2 | * | 4/2004 | Timm et al. | .................. 606/169 |

* cited by examiner

*Primary Examiner*—Leslie R Deak

(57) ABSTRACT

The fitment is an elongated connector providing a conduit for aspirant to flow from a pump cartridge to an interior of the collection bag. The connector has a first end configured for attachment to the pump cartridge and a second end for positioning within the interior of the collection bag. The second end also includes at least one notch formed in the connector. The notch acts to prevent the collection bag from sealing off the conduit during surgery so that a sufficient amount of air will remain within the bag to allow a surgeon to air vent an aspiration path during surgery.

4 Claims, 8 Drawing Sheets

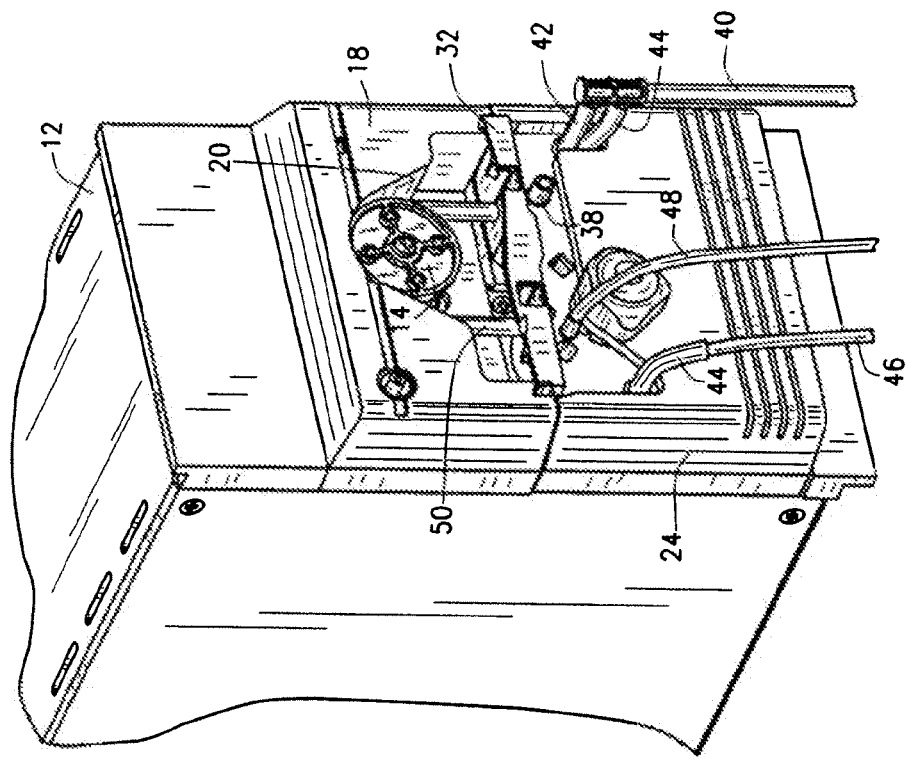
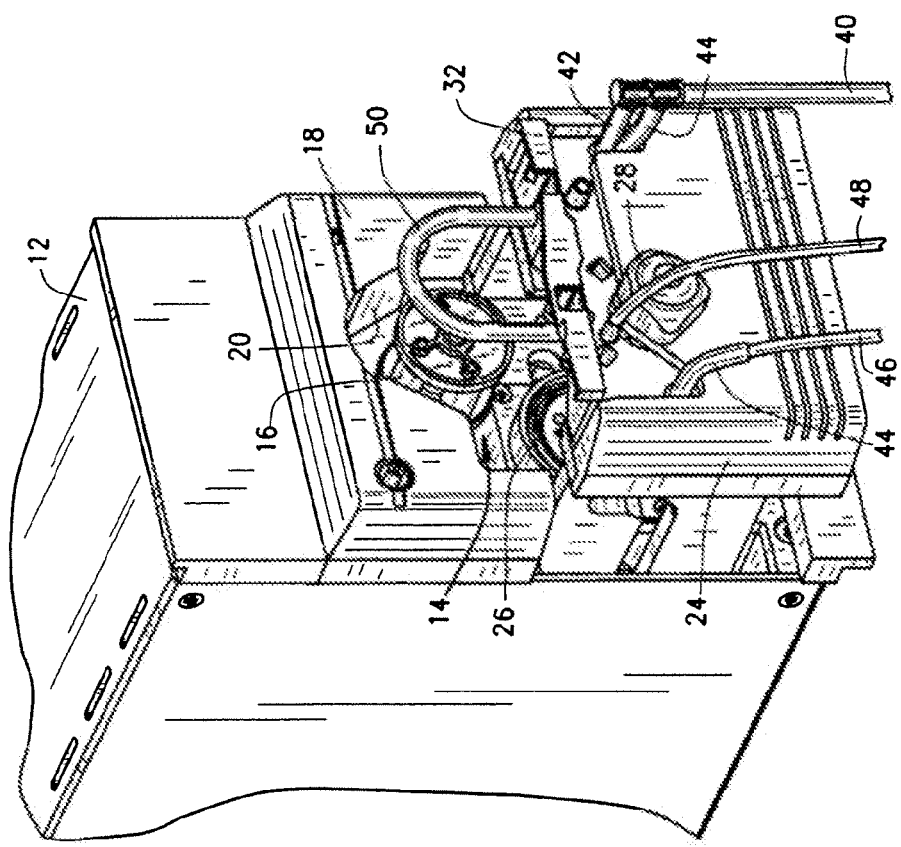
FIG. 4
FIG. 3

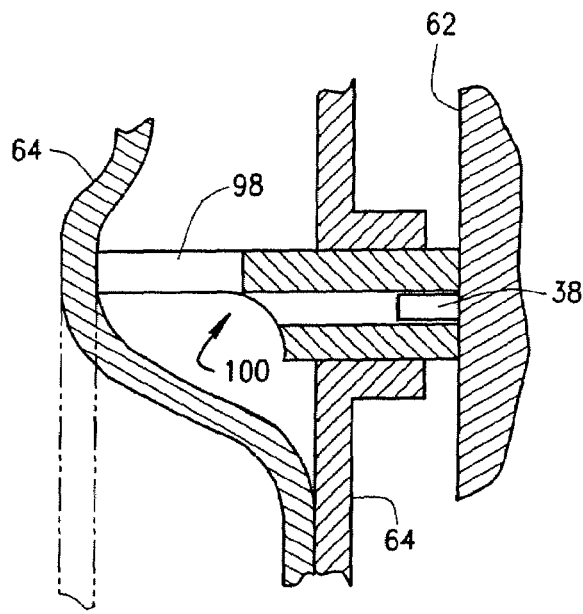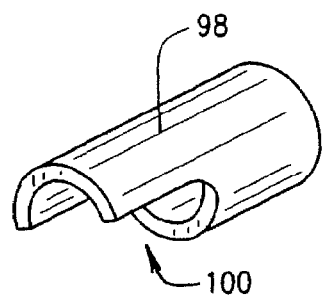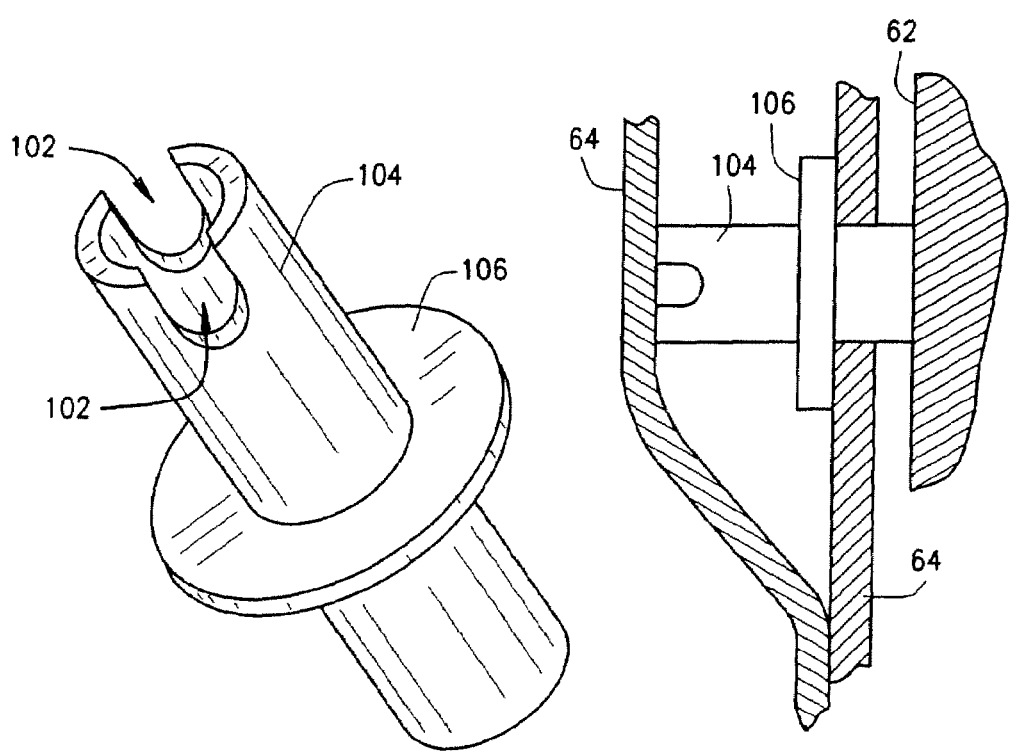
FIG. 11　　FIG. 12
FIG. 13　　FIG. 14

PERISTALTIC PUMP FITMENT FOR ATTACHMENT TO AN ASPIRANT COLLECTION BAG

BACKGROUND OF THE INVENTION

1. Field of the Invention

The present invention relates to cartridges for peristaltic pumps having removable collection bags. More particularly, the present invention relates to peristaltic pumps having air venting capabilities.

2. Description of Related Art

During use of a peristaltic pump during surgery an occlusion of the aspiration path may occur. Upon experiencing an occlusion a vacuum level in the aspiration path will continue to build because the pump continues to attempt to pump aspirant through the aspiration path and into a collection bag. In order to relieve this vacuum and stabilize the aspiration path it is well known to air vent the aspiration path.

Typically air venting is accomplished by attaching one end of a length of tubing to the aspiration path with the other end exposed to the atmosphere. However, it is also known to air vent via a closed bag system where the air to vent the aspiration path is obtained from the collection bag. In order to ensure that a sufficient amount of air is available to vent the aspiration path it has been known to place a spacer element within the bag. The spacer elements used include sponges or some rigid structure to spread the bag apart and provide an air space within the bag.

These spacer elements are effective but are cumbersome to manufacture and more expensive to make than if these separate elements were not required.

Therefore, it would be desirable to provide a collection bag that accommodates air venting without the need for the separate spacer elements.

BRIEF DESCRIPTION OF DRAWINGS

FIG. 3 is the same view as FIG. 2 with a portion of the cartridge removed;

FIG. 4 is the same view as FIG. 3 with the drawer closed and the pump head in a tubing engaged position;

FIG. 11 is a partial cut-away view showing a collection bag assembly in accordance with the present invention;

FIG. 12 is a perspective view of a fitment of FIG. 11 without the collection bag attached;

FIG. 13 is a perspective view of an alternative embodiment of a fitment in accordance with the present invention; and FIG. 14 is a partial cut-away view with the fitment of FIG. 13 attached to a collection bag and pump cartridge.

DETAILED DESCRIPTION OF THE PREFERRED EMBODIMENT

Figure 1:
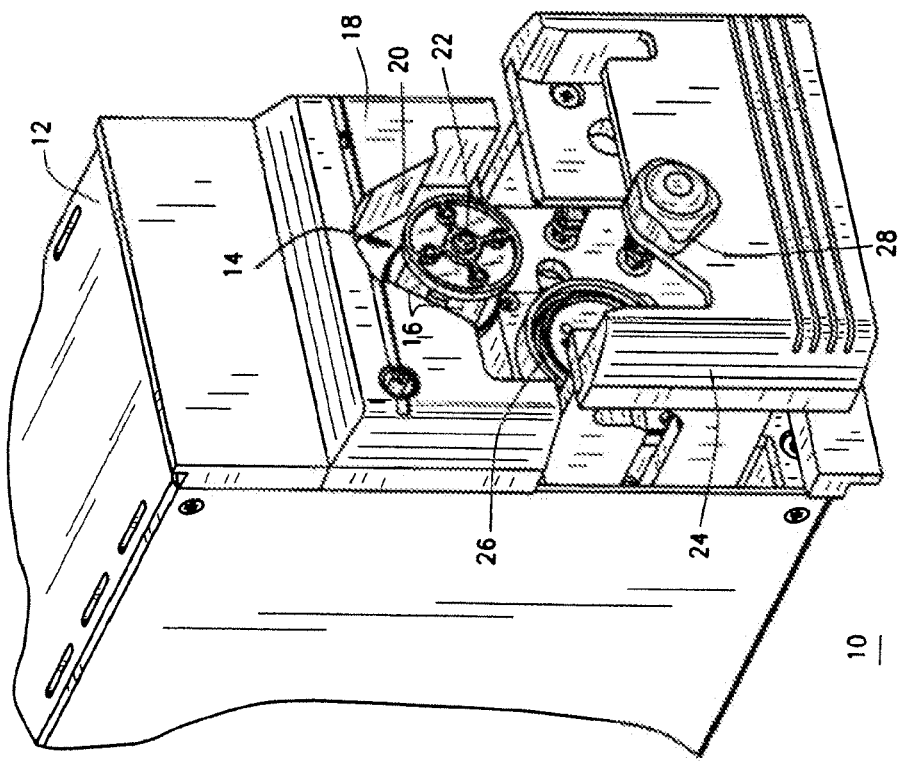
FIG. 1 is a partial perspective of a peristaltic pump in accordance with the present invention.

FIG. 1 shows a partial perspective view of a peristaltic pump 10 for use in ophthalmic surgery, in accordance with the present invention. A housing 12 includes a pump head 14 having a plurality of rollers 16 held within and extending from the housing 12. A backing plate 18 is attached to the housing 12 and cooperates with the pump head 14 to pinch a length of tubing between the rollers 16 and backing plate surface 20. Pump head 14 moves relative to the housing 12 and the backing plate 18, as described in detail below. In FIG. 1, pump head 14 is shown in an open position and ready for the insertion of a pump cartridge, as described below.

Pump head 14 is preferably connected to a motor (not shown) and the pump head 14 causes rollers 16 to rotate about a central axis 22 of the pump head 14, such that the rollers 16 and the backing plate 18 cooperate to compress or pinch a length of surgical tubing and peristaltically pump fluids from a surgical site through the tubing to a collection bag, as described in further detail below. Pump head 14 preferably moves or translates in a straight line towards and away from the backing plate 18. Pump head 14 can be made to move by any manner known to those skilled in the art, such as by pneumatic or hydraulic pistons, or stepper motors, or other known means. In addition, pump head 14 may include various numbers of rollers 16, depending on the desired head 14 size and the performance requirements to be obtained.

Peristaltic pump 10 preferably further includes a cartridge-holding drawer 24 for insertion of a pump cartridge, as shown in more detail below. In addition, pump 10 further includes a pressure transducer interface 26 and spring housing 28 for urging a pressure transducer and a pump cartridge against pressure transducer interface 26.

Figure 2:
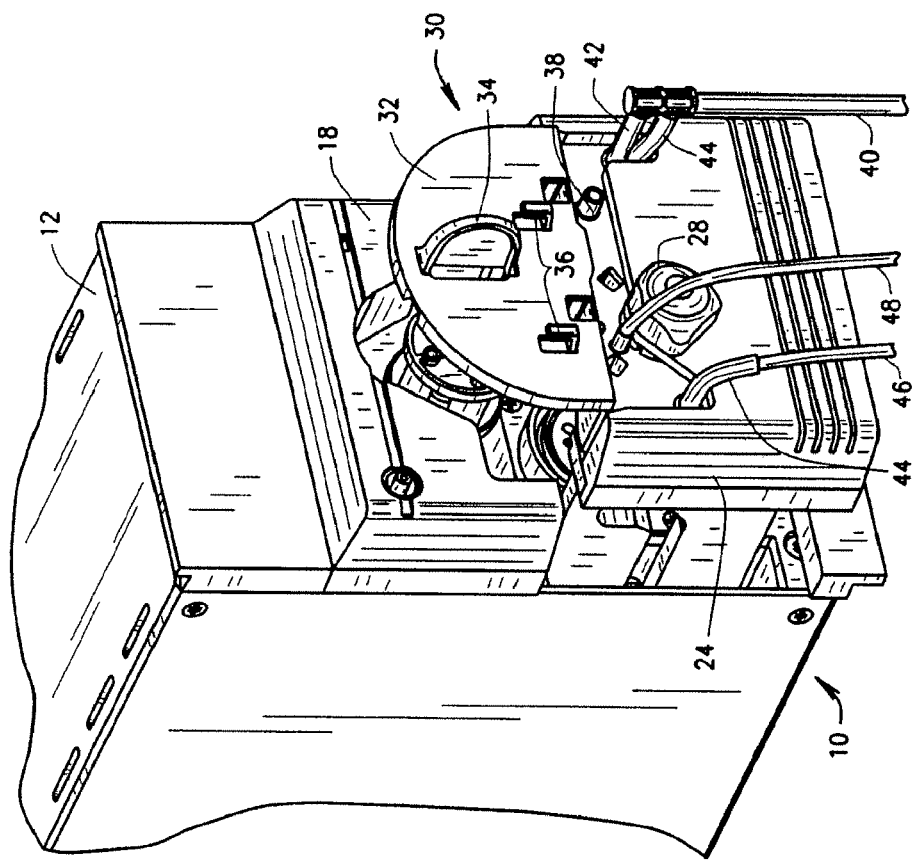
FIG. 2 is the pump of FIG. 1 with a pump cartridge inserted into a drawer of the inventive pump.

FIG. 2 is similar to FIG. 1 with the addition of a pump cartridge 30 inserted into cartridge drawer 24. Pump cartridge 30 includes a housing with an upper portion 32 including a handle 34 for assisting a user in inserting and removing the cartridge 30 from drawer 24. Pump cartridge 30 of FIG. 2 is shown without a collection bag in order to reveal further details of the cartridge 30 and pump 10. The collection bag typically hangs from hooks 36 in front of the drawer 24. Aspirant (fluids and tissue) flows through fitment or barb 38 to the collection bag (not shown) for collecting fluids and tissue from a surgical site. Preferably, the cartridge housing, including upper portion 32, is formed of a molded plastic material, such as acrylonitrile-butadiene-styrene (ABS) or other.

Connected to pump cartridge 30 is an irrigation line 40, which is typically connected to a bottle or bag of balanced salt solution (BSS) (not shown). Irrigation line 40 is then connected to fluid venting conduit or tube 42 and to a second irrigation line 44 which extends across pump cartridge 30, as shown in further detail below to provide for a control valve, typically a pinch valve (not shown), that opens and closes irrigation line 44. Irrigation line 44 is then connected to a further length of tubing 46 that ultimately is connected to a surgical handpiece, such as a phacoemulsification (phaco) handpiece or other irrigation device for use in ophthalmic surgery. An aspiration line 48 is also connected to pump cartridge 30 which carries aspirant from a surgical handpiece.

FIG. 3 is similar to FIG. 2, except that upper portion 32 of pump cartridge 30 is partially cut-away to provide a detailed view of resilient surgical tubing 50 which cooperates with rollers 16 and backing plate 18 surface 20 to pump aspirant through line 48 and to the collection bag (not shown). One of the main advantages of pump head 14 moving or translating relative to the housing 20 is that when the pump head 14 is in an open position, as shown in FIG. 3, the surgical tubing 50 is easily inserted between the pump head 14 and the backing plate 18. Pump head 14 should be in a position, such that the loop of tubing 50 easily clears pump head 14.

When door or drawer 24 closes and pump head 14 translates from the open position, shown in FIG. 3, to an operative or closed position, shown in FIG. 4, and the pump head 14 is rotated, the rollers 16 and the backing plate surface 20 cooperate to compress the tubing 50 to peristaltically pump aspirant from a surgical site through the tubing 50 and 48. Aspirant flows through tube 48 to tube 50 and out barb 38 to a collection bag not shown.

After the cartridge or cassette holder drawer 24 moves from the open position of FIG. 3 to the operative position of FIG. 4, the pump head 14 is moved toward the backing plate 18, such that the rollers 16 and the backing plate surface 20 cooperate to peristaltically pump aspirant through the length of tubing 50 as the pump head 14 is rotated. Additional tubing 48 is typically connected to a surgical aspiration device, such as a phacoemulsification handpiece for peristaltically pumping aspirant through the tubing from a patient's eye during surgery.

In this way, it can be seen that by having pump head 14 move relative to the backing plate 18 and the housing 12, a length of surgical tubing 50 attached to a pump cartridge 30 is then easily inserted between the rollers 16 and backing plate surface 20. The present invention does not rely on complicated threading mechanisms, such as found in the prior art nor does the present invention require the pump cartridge 30 to be grasped and pulled away from the pump head in order to stretch tubing across the pump head as also found in the prior art.

Figure 5:
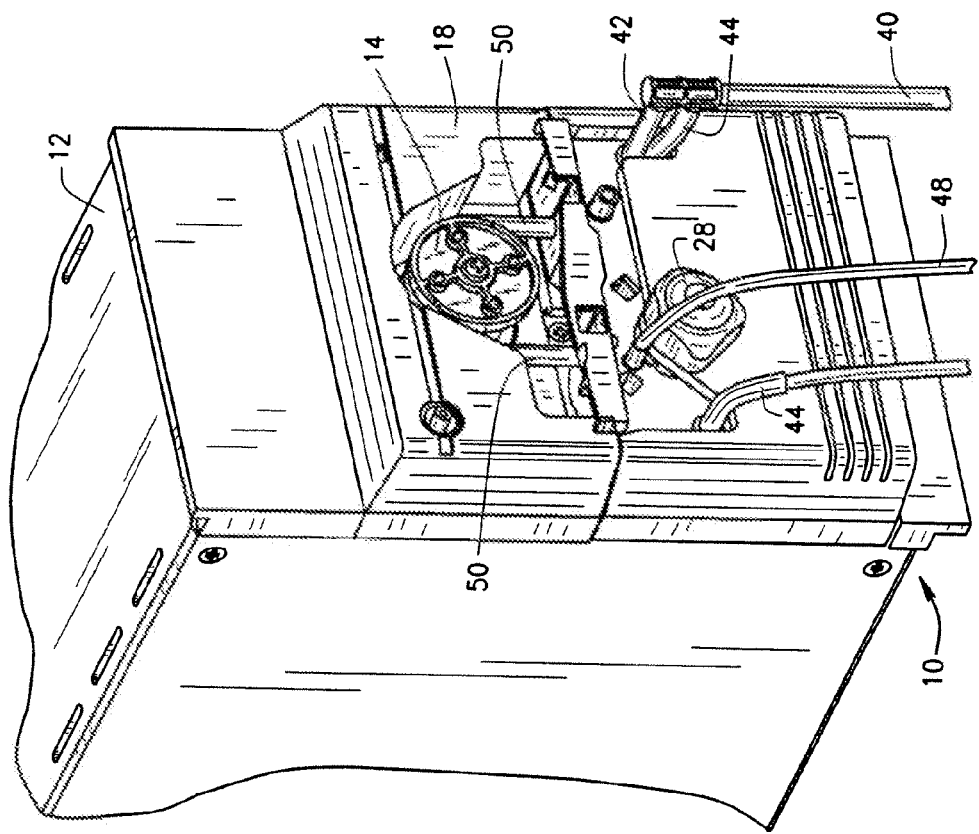
FIG. 5 is similar to the view of FIG. 4, except the pump head has been moved to a tubing vent position.

FIG. 5 shows the pump 10 in an air vent position, which is yet another inventive aspect of the present invention. FIG. 5 is different from the open position of FIG. 3 and the operative position of FIG. 4, in that the pump head 14 is in a position intermediate of those positions shown in FIGS. 3 and 4. That is to say, pump head 14 has been moved away from backing plate 18 a sufficient distance to allow tubing 50 and 48 to be air vented upon the occurrence of an occlusion. In operation when a surgeon experiences an occlusion in the aspiration line 48 or at the tip of his phaco handpiece, he will typically activate a button on a control panel, release a foot pedal (both not shown), or trigger a software control, causing pump head 14 to momentarily move away from backing plate 18, as shown in FIG. 5. For instance, when a drastic change in vacuum is detected, the head is dropped to avoid a post-occlusion surge, regardless of user input. This temporary pump head movement allows the vacuum built-up in the aspiration path to be relieved by removing the pinch points created in the operative position by rollers 16 and backing plate 18. This allows the vacuum to be relieved via air contained in the collection bag (not shown). Pump head 14 is preferably only momentarily moved away from backing plate 18 and only for a sufficient amount of time to relieve the vacuum, typically less than one (1) second. It would not be desirable to allow pump head 14 to remain in its air vent position of FIG. 5 for an extended period of time, because all the aspirant in lines 50 and 48 would begin leaking back out of the aspiration device and into the eye. Of course, this is not a concern if as is know, a pinch valve operates to close the aspiration line during venting.

Figure 6:
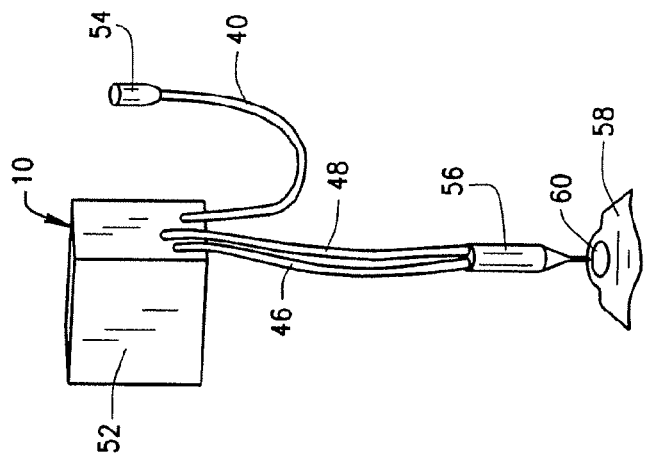
FIG. 6 is a partial block diagram showing the use of a peristaltic pump in accordance with the present invention connected to a surgical console and in use during surgery.

FIG. 6 shows a block diagram of the pump 10 in use with an ophthalmic surgical system, such as the Millenium™ System available from Bausch & Lomb. The system typically includes pump 10 incorporated into a control console 52, which controls the operation of pump 10. FIG. 6 also shows irrigation line 40 connected to an irrigation source, such as BSS bottle 54. In addition, the connection of irrigation line 40 and aspiration line 48 to the ophthalmic surgical handpiece 56 is shown. Handpiece 56 is typically a phaco device inserted into eye 58 for removing a cataract 60 or for performing other ophthalmic surgery. This simple method of air venting the aspiration line enables a vacuum to be quickly and efficiently removed from the aspiration path defined by a handpiece 56, aspiration tubing 48, and the aspiration tubing loop 50. Typically, the prior art uses a pinch valve associated with a short section of tubing open to the atmosphere at one end and connected to the aspiration line on the other end.

One aspect of the present invention, by using the advantage of the moveable pump head, allows for the elimination of the prior art pinch valve for air venting (thus, reducing costs of manufacture) and allows the venting to occur in a very short time period. This short venting duration reduces the amount of air introduced to the aspiration line and helps control an undesired surge of aspirant through the aspiration path, as compared to the prior art. Another way of describing the inventive air venting feature is to say the pump head 14 or the backing plate 18 is moveable from a tubing pinched or engaged position to a tubing vent position such that the tubing is vented by removing the pinch between the rollers 16 and the backing plate 18. In one embodiment of the invention, the pump head 14 is moveable to a vent position while the rollers 16 are rotating. In other embodiments the pump head may completely stop before moving to a vent position.

Figure 7:
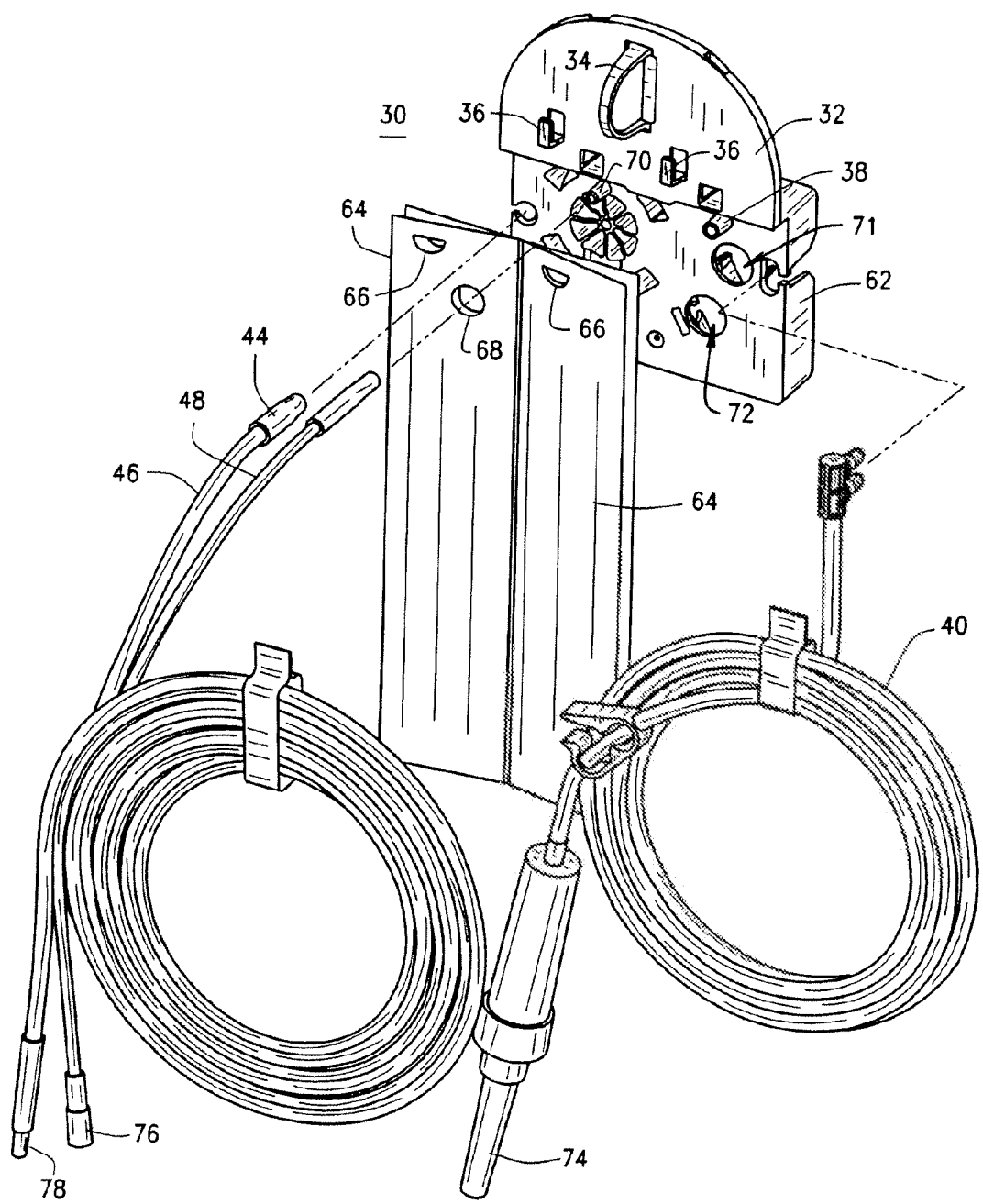
FIG. 7 is an exploded perspective view of an inventive peristaltic pump cartridge in accordance with the present invention.

FIG. 7 is an exploded perspective view of pump cartridge 30. Pump cartridge 30 includes a molded housing 62 including upper portion 32 with handle 34. Hooks 36 preferably hold collection bag 64 via openings 66. As can be seen, aspiration line 48 also passes through an opening 68 for connection to the pump housing 62 at barb 70. Collection bag 64 is preferably formed of a flexible, liquid-tight material for collecting aspirant from a surgical site through barb 38. Preferably, collection bag 64 is formed of a co-layer of nylon and polyethylene to provide for a strong, yet inexpensive bag that can be easily connected to a fitment, as described in detail below. Collection bag 64 is more precisely a collection bag assembly 64 because attached to collection bag 64 is a fitment described in detail below. Those skilled in the art will appreciate that, collection bag 64 could also be other types of containers such as a rigid cassette, or a bottle, or other reservoir suitable for collecting aspirant from a surgical site. It is also preferred that collection bag 64 be large enough to hold aspirant from a typical surgery on at least one eye.

As is known in the prior art, it is preferred that aspirant line 48 be as non-compliant as possible, that is, as stiff and rigid as possible to prevent and minimize the collapse of tubing 48 upon the occurrence of an occlusion and the build-up of vacuum in the aspiration path. Housing 62 also preferably includes openings 71 and 72 to allow for operation of pinch valves (not shown), as is well known in the art. The operation of the pinch valve with relation to opening 71 will be described in detail below. Opening 72 is associated with irrigation line 40 and 44. Typically, a pinch valve of pump 10 passes through opening 72 and causes the opening and closing of irrigation tubing 44 to control the flow of BSS through irrigation line 40 and 46 to a handpiece not shown. End 74 of irrigation line 40 is typically connected to a BSS bottle as previously shown in FIG. 6. End 76 of aspiration line 48 and end 78 of irrigation line 46 are typically connected to a surgical handpiece, such as a phaco handpiece for use in surgery.

Figure 8:
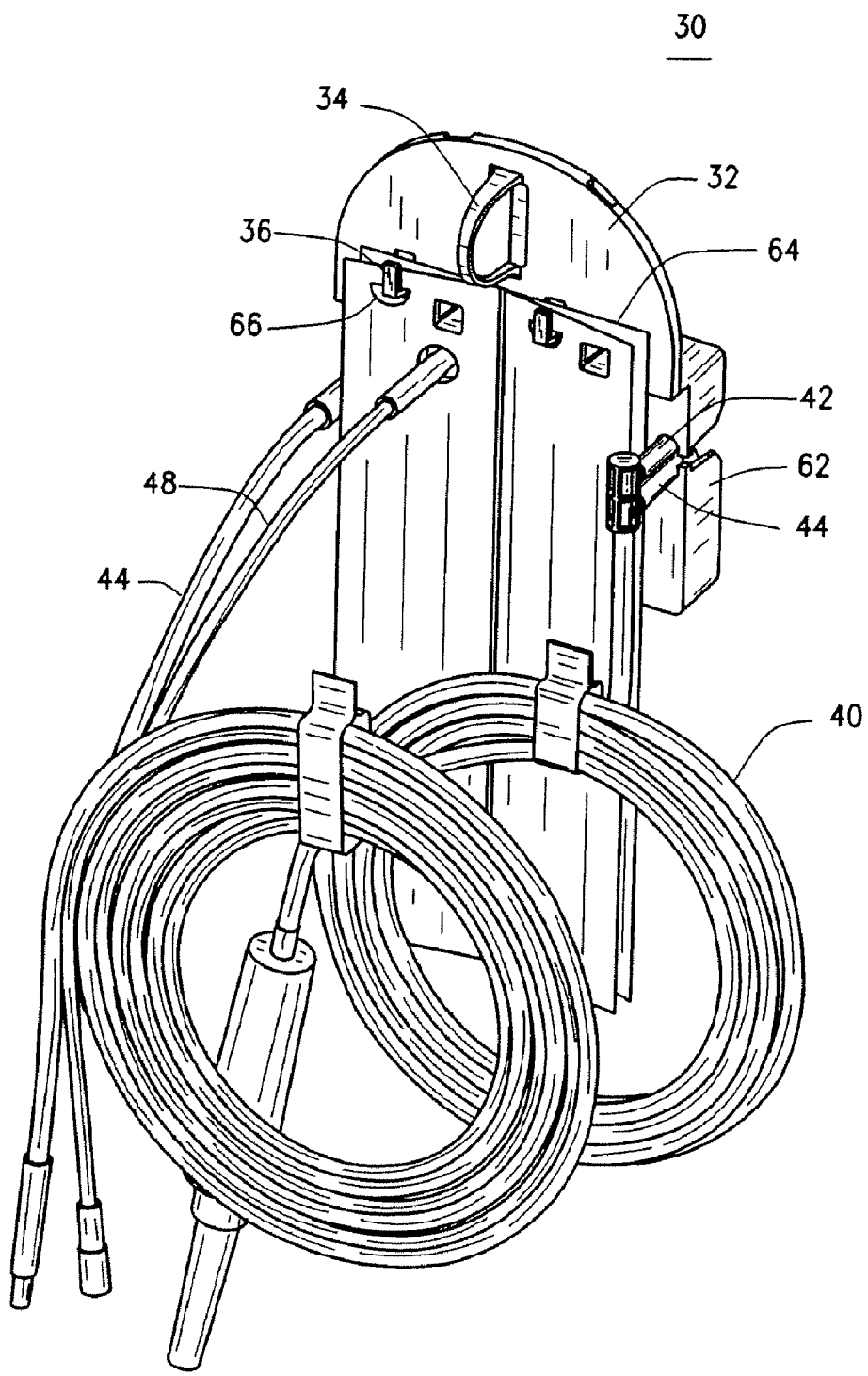
FIG. 8 is a perspective view of a pump cartridge in accordance with the present invention.

FIG. 8 shows a perspective view of the pump cartridge 30 fully assembled, including irrigation line 40, fluid venting line 42, irrigation lines 44 and 46, aspiration line 48, and collection bag 64.

Figure 9:
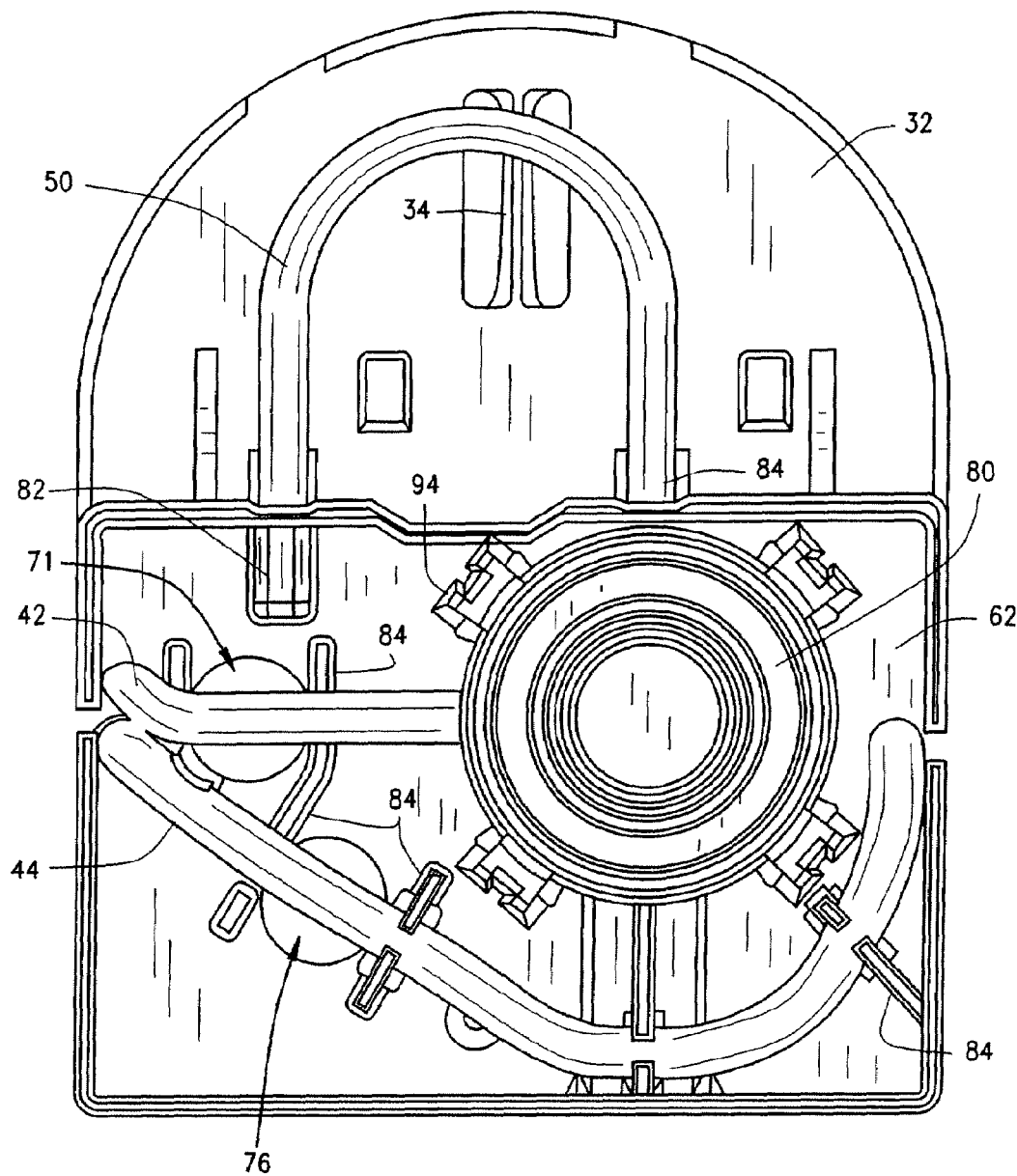
FIG. 9 is an elevation of a portion of a pump cartridge in accordance with the present invention.

FIG. 9 is an elevation view of an opposite side of the cartridge 30 and housing 62 from that shown in FIGS. 7 and 8. Pump loop 50 is shown with one end 82 connected to the collection bag via barb 38 and the other end 84 connected to both aspiration line 48 and diaphragm pressure transducer assembly 80. Pressure transducer 80 preferably detects the pressure in aspiration line 48 and tubing 50 by deflection of the diaphragm 90 (separately shown is FIG. 10). Diaphragm 90 deflects to indicate a change in pressure. Diaphragm 90 may deflect as much as 5 thousandths of an inch at 550 mmHg (millimeters of mercury). Preferably, housing 62 includes tube holders 84 molded into the housing for holding the lengths of tubing within the cartridge, as shown in FIG. 9.

Irrigation line 42 and opening 71 cooperate with a pinch valve not shown to fluidly vent pressure transducer 80 when commanded by console 52. The pinch valve operates to control the flow of irrigation fluid to the pressure transducer 80. A high vacuum is typically caused by an occlusion occurring within the eye being operated on when the aspiration port of the surgical handpiece is closed off or occluded by tissue. As the occlusion happens, the pump head 14 continues to attempt to pump aspirant through the aspiration path and into collection bag 64.

As explained above, the tubing loop 50 may be air vented by the movement of the pump head. Of course, the tubing 50 may also be air vented by the movement of the backing plate, though this is not shown. Those skilled in the art will readily recognize that the movement of backing plate 18 away from pump head 14 will also allow tubing 50 to become unpinched and therefore, vent air from the collection bag 64 to relieve the vacuum that has been created in aspiration line 48 and the surgical handpiece. In certain circumstances, it may be preferred to vent the aspiration path with liquid rather than air and liquid venting tube 42 and opening 71 cooperate with a pinch valve not shown to vent fluid directly to pressure transducer 80.

The prior art teaches fluid venting by venting fluids to the aspiration line 48; however, the most compliant portion of the aspiration path and that portion which displaces the most volume is the pressure transducer 80. By directly venting fluid to the pressure transducer 80, that portion of the aspiration path that is the most compliant and displaces the most volume upon the occurrence of an occlusion is most quickly stabilized by directly venting fluid to the pressure transducer 80. Directly venting to the pressure transducer 80 minimizes post occlusion surge, which is highly undesirable and, it is believed, the aspiration path is stabilized more quickly than known in the prior art. Pressure transducer 80 is preferably connected between a handpiece 56, as shown in FIG. 6, and a collection bag or reservoir 64. This allows the pressure transducer 80 to provide a user, through the pressure transducer interface 26, with an accurate reading of the pressure being experienced in the aspiration path. Pressure transducer 80 is preferably similar to that described in U.S. Pat. Nos. 5,746,719 and 5,753,820, although other types of pressure sensors may also be used such as other diaphragm sensors or piezoelectric sensors.

Figure 10:
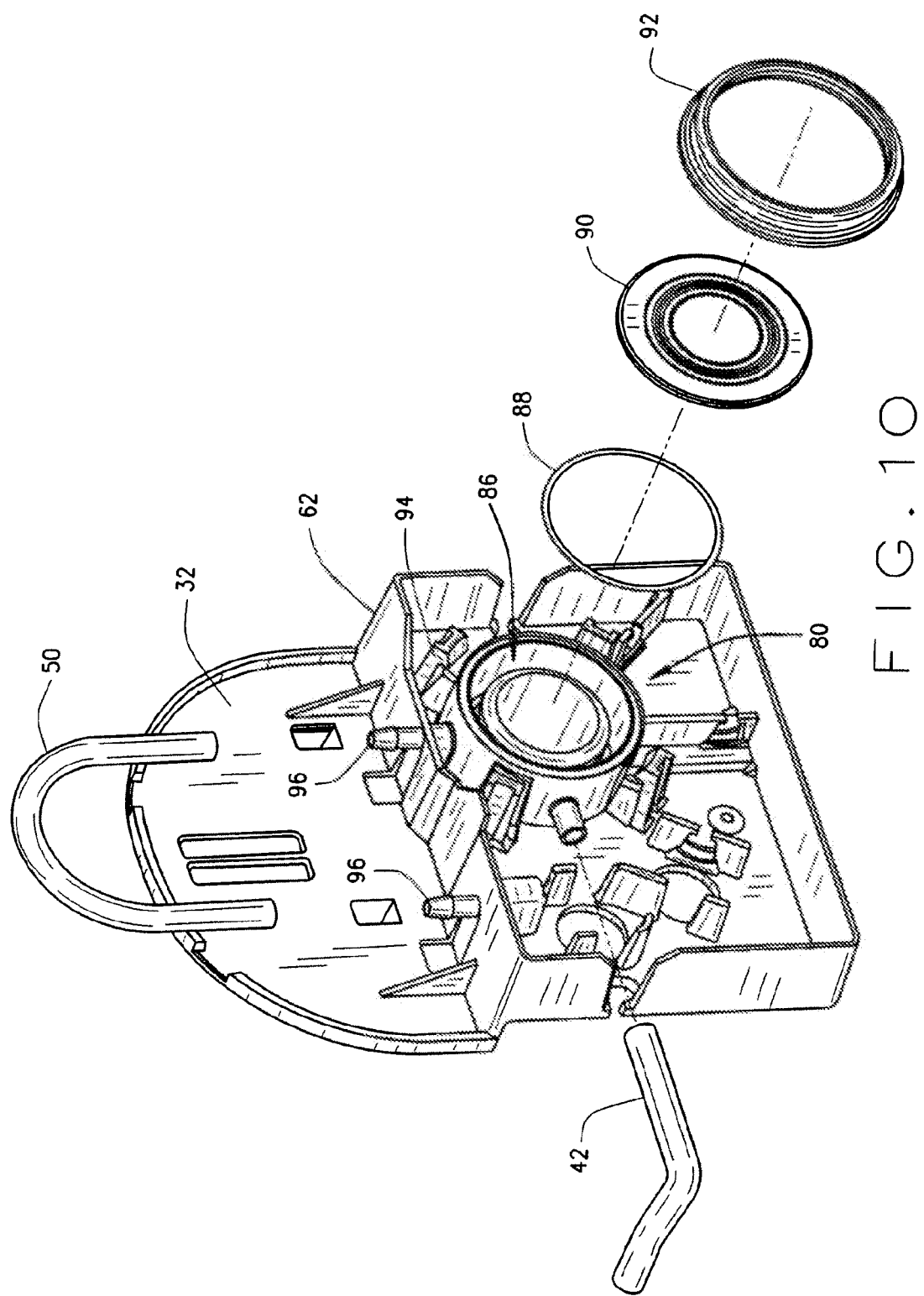
FIG. 10 is an exploded perspective view of a portion of a pump cartridge in accordance with the present invention.

FIG. 10 shows an exploded perspective view of the housing 62 and some of the components connected to the housing 62. For instance, pressure transducer 80 includes an internal volume portion 86 molded into housing 62. In addition, pressure transducer 80 preferably, includes an o-ring 88 for fluidly sealing a diaphragm 90 to the internal volume portion 86 via snap ring 92, which is held in housing 62 via arms 94. FIG. 10 also shows the connection of fluid venting conduit or tubing 42 to the pressure transducer 80. The connection of pump tubing length 50 to barbs 96 is shown. Barbs 96 are preferably molded into housing 62. It is preferred that barbs 96 be unitarily molded, so as to avoid formation of parting lines on barbs 96, which can lead to aspirant leaking from within tubing 50.

FIGS. 11-14 show two (2) embodiments of an inventive fitment for attachment to collection bag assembly 64. FIG. 11 is a partial cut-away view of an inventive collection bag 64 and fitment 98 for use with the pump cartridge 30. Fitment 98 is preferably an elongated connector attached to collection bag 64 and connects to cartridge 62 at fitment or barb 38 as shown. Fitment 98 has opposing ends. A first end is structured for attachment to the pump cartridge 30 and the second end is positioned within the interior of bag 64. Collection bag 64 may be sealed to fitment 98 by prior art means, such as adhesive. However, fitment 98 is preferably formed of a polyethylene material similar to that forming a layer of collection bag 64 and in this manner, collection bag 64 may be heat-sealed to fitment 98, such that no adhesive is required to form a liquid-tight seal between the bag and the fitment. This results in the elimination of toxic adhesives and provides a simpler, more efficient means of attaching fitment 98 to collection bag 64.

It is possible to form fitment 98 and collection bag 64 of materials other than polyethylene. However, in order to avoid the use of adhesives, it is important to use materials that have essentially the same co-efficient of expansion. Upon the introduction of heat, both materials should begin to melt at approximately the same temperature, and therefore, after the heat is removed, a seal will form between the bag and fitment. Fitment 98 provides a conduit for aspirant flow from the pump cartridge 62 to an interior of the bag 64.

A further inventive feature of fitment 98, is best shown in the perspective view of FIG. 12, and is notched portion 100. As can be seen in FIG. 11, notched portion 100 ensures that as a vacuum is pulled through the aspiration path as explained above, the collection bag 64 cannot completely collapse around the opening in fitment 98 to seal-off fitment 98. This notch 100 ensures that a sufficient amount of air will be contained within collection bag 64 to vent any inappropriately high vacuum level that has built up in the aspirant path, including tube 50, pressure transducer 80, or aspiration line 48. The prior art typically relied on the use of some spacer member to be inserted within bag 64, such as a piece of foam or resilient wiring. The provision of the notch 100 in fitment 98 allows for the elimination of the foam or other spacer elements within bag 64 and therefore, provides for a cheaper more efficiently manufactured collection bag than possible in the prior art.

FIGS. 13 and 14 show an alternate embodiment of the notched fitment of FIGS. 11 and 12. FIG. 13 shows the formation of opposing notches 102 within a fitment 104. Fitment 104 also preferably includes an attachment ring 106 that provides a convenient flat surface for attaching bag 64 to fitment 104 via heat sealing as described above. Fitment 104 is also constructed to mate with barb 38 and is also preferably formed from polyethylene, as described above.

The fitments 98 and 104 allow the collection bag 64 to be removed from cartridge 30 during surgery. This is highly desirable because a collection bag 64 may fill up prior to the end of surgery and changing collection bags is more efficient and less expensive than placing a new cartridge into the pump 10.

Thus, there has been shown and described a novel pump, cartridge, and venting methods. Variations and alternate embodiments will be apparent to those skilled in the art without departing from the scope of the claims that follow. For instance, it will be apparent to those skilled in the art, that if a prior art peristaltic pump that does not require a backing plate is used (as described above), the inventive air venting can still be utilized by simply momentarily relieving the strain on the stretched loop of tubing to remove the pinch points created by the pump head rollers.

We claim:

1. A fitment for attachment to an ophthalmic aspirant collection bag comprising:

an elongated connector connected to a ophthalmic pump cartridge providing a conduit for aspirant to flow from the pump cartridge to an interior of the collection bag;

the connector having opposing ends wherein a first end is structured for attachment to the pump cartridge and a second end positioned within the interior of the collection bag is structured to form at least one notch in the second end of the connector; and wherein the notch acts to prevent the collection bag from sealing off the conduit during surgery so that a sufficient amount of air will remain within the bag to allow a surgeon to air-vent an aspiration path during surgery to prevent collapse of an eye of a patient.

2. The invention of claim 1, wherein the fitment and the collection bag are heat-sealed together, such that no adhesive is required to form a liquid-tight seal between the bag and the fitment.

3. The invention of claim 2, wherein a sealing-ring is formed between the opposing ends for providing a surface to seal the bag to the fitment.

4. The invention of claim 1, wherein the second end includes two notches formed in opposing sides of the second end.

* * * * *